(12) United States Patent
Nestleroth et al.

(10) Patent No.: US 7,218,102 B2
(45) Date of Patent: May 15, 2007

(54) PIPELINE INSPECTION APPARATUS AND METHOD

(75) Inventors: John B. Nestleroth, Westerville, OH (US); Richard J. Davis, III, Columbus, OH (US); Ronnie D. Gallliher, Baltimore, OH (US); George N. Brand, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 65 days.

(21) Appl. No.: 10/960,739

(22) Filed: Oct. 7, 2004

(65) Prior Publication Data
US 2006/0076951 A1 Apr. 13, 2006

(51) Int. Cl.
*G01N 27/82* (2006.01)
*G01N 27/90* (2006.01)

(52) U.S. Cl. .................. 324/240; 324/220; 324/232; 324/242

(58) Field of Classification Search ............... 324/240, 324/220, 232, 242
See application file for complete search history.

(56) References Cited

U.S. PATENT DOCUMENTS

| | | | |
|---|---|---|---|
| 3,060,377 A | 10/1962 | Schmidt | |
| 3,745,452 A | 7/1973 | Osburn et al. | |
| 4,153,875 A | 5/1979 | Pigeon et al. | |
| 4,427,940 A | 1/1984 | Hirama et al. | |
| 4,439,730 A | 3/1984 | Kauffman | |
| 4,468,619 A | 8/1984 | Reeves | |
| 4,652,820 A | 3/1987 | Maresca | |
| 4,789,827 A | 12/1988 | Bergander | |
| 5,269,916 A * | 12/1993 | Clair | 210/222 |
| 5,293,117 A | 3/1994 | Hwang | |
| 5,357,198 A | 10/1994 | Ando et al. | |
| 5,502,382 A | 3/1996 | Ando et al. | |
| 5,512,821 A | 4/1996 | Ando et al. | |

(Continued)

FOREIGN PATENT DOCUMENTS

GB 1567166 5/1980

(Continued)

OTHER PUBLICATIONS

Atherton, David L. et al.; Stress Induced Magnetization Changes of Steel Pipes—Laboratory Tests; IEEE Transactions on Magnetics; vol. Mag-19, No. 4; Jul. 1983; pp. 1564-1568.

(Continued)

*Primary Examiner*—Reena Aurora
(74) *Attorney, Agent, or Firm*—Barry S. Bissell; Todd J. Harrington; William B. Richards

(57) ABSTRACT

A apparatus for pipeline integrity monitoring comprising a magnetically permeable backing bar and at least three magnets comprising a relatively medium-strength magnet positioned at one end of the backing bar, a relatively low-strength magnet positioned at the other end of the backing bar, and a relative high-strength magnet positioned between the medium-strength and the low-strength magnet. The at least three magnets are adapted and positioned to induce a plurality of resultant fields within the pipeline wall comprising a first resultant field suitable for detecting a reduced metal-related anomaly and a second resultant field suitable for detecting a mechanically worked-related anomaly. Preferably, the first resultant field has a strength greater than 120 Oersted and the second resultant field has a strength between 40 and 80 Oersted.

27 Claims, 11 Drawing Sheets

U.S. PATENT DOCUMENTS

| | | | |
|---|---|---|---|
| 5,606,260 | A | 2/1997 | Giordano et al. |
| 5,751,144 | A | 5/1998 | Weischedel |
| 5,864,232 | A | 1/1999 | Laursen |
| 6,057,684 | A | 5/2000 | Murakami et al. |
| 6,100,684 | A | 8/2000 | Ramaut |
| 6,265,870 | B1 | 7/2001 | Weischedel |
| 2002/0011124 | A1 | 1/2002 | Phipps |
| 2003/0011363 | A1 | 1/2003 | Wayman et al. |

OTHER PUBLICATIONS

Bubenik, T.A. et al.; Multiple Magnetization Level MFL For Pipeline Mechanical Damage Characterization; Internation Pipeline Conference; Oct. 1-2, 2000; Calgary, Alberta, Canada, pp. 1-7.

Bubenik, T.A. et al.; In-Line Inspection Technologies for Mechanical Damages & SCC in Pipelines-Final Report for US Dept of Transporation; Off. of Pipeline Safety; Jun. 2000, pp. i-vi, pp. 1-249.

Davis, Richard J. et al.; Pipeline Mechanical Damage Characterization By Multiple Magnetization Level Decoupling; Report for US Dept of Transportation Off. of Pipeline Safety, 8 pages, no date.

Dobmann, G. et al.; Physical Analysis Methods of Magnetic Flux Leakage; Research Techniques in Nondestructive Testing; vol. IV; Chapter 2; 1980; Academic Press; pp. 39-69.

Nestleroth, J.B. et al.; Magnetic Flux Leakage (MFL) Technology For Natural Gas Pipeline Inspection; Prepared for The Gas Research Institute; Feb. 1999, 37 pages.

Nestleroth, J.B. et al.; Stress, Cold Work and Metal-Loss Induced Magnetic Flux Leakage Signals; Proceedings of 11th PRCI-EPRG Joint Technical Meeting on Pipeline Research; Published by PRCI, Arlington, VA; Apr. 1997, 14 pages.

Nestleroth, J.B. et al.; Variation of Magnetic Properties in Pipeline Steels; Report for US Dept of Transportation Off. of Pipeline Safety; Nov. 1997, pp. 1-v and 101 pages.

* cited by examiner

PIPELINE INSPECTION APPARATUS AND METHOD

This invention was made with Government support under Agreement No. DTRS56-02-T-0002 awarded by the Department of Transportation, RSPA. The Government may have certain rights to this invention.

FIELD OF THE INVENTION

This invention relates generally to apparatus designed and operated to inspect magnetically permeable objects, pipeline walls for example, for corrosion and mechanical damage as well as other anomalies and defects such as cracks and pitting. More particularly, this invention relates to pipeline inspection apparatus which utilize magnetic field leakage ("MFL") in pipeline integrity management programs.

BACKGROUND OF THE INVENTION

Much of the lifeblood of the world economy flows through pipeline transportation systems. Large volumes of products as diverse as petroleum and liquid hydrocarbons, natural gas, propane, and slurries of solids such as granulated coal and minerals such as copper and iron are constantly being transported between production sites and processing and consumption sites over long distances. These pipelines range generally between 12 inches and 60 inches in diameter and extend to thousands of miles in length. In addition, there are curves and bends along the pipeline with radii of curvature of generally about three times the pipeline diameter, though tighter bends are possible. Usually constructed of metal, in particular, ferrous metals, pipelines are susceptible to damage and other defects which affect the integrity of the system. The result can be a failure which threatens life and property, serious environmental damage, disruptions to both local and distant economies, and loss of the product being transported. The further result can be reduced public confidence in this efficient and economic means of transporting materials with possible public opposition to the growth of such means.

To minimize the risk of failure, pipelines are closely monitored and inspected. One inspection method utilizes pipeline inspection apparatus which are inserted into the pipeline and move through the pipeline generally, but not exclusively, via the flowing material in the pipeline. Such pipeline inspection apparatus may comprise magnetic components to induce magnetic flux (commonly illustrated by lines) within the pipeline wall. The magnetic flux naturally enters the metal wall of the pipeline and distributes evenly to produce a full volumetric inspection. Anomalies or defects in the wall of the pipeline tend to disrupt the uniform flow of the flux and create a leakage of magnetic flux which can then be detected by sensors, generally within the apparatus itself. This inspection methodology is known as magnetic flux leakage ("MFL"). MFL-based apparatus have the capability of addressing, with gas pipelines for example, nearly all the threats listed in ASME B31.8S except incorrect operation and incorrect equipment.

Other inspection methods include, for example, inducing eddy currents in the pipeline via the placement of an auxiliary magnetic pole and relative movement of the inspection apparatus and the pipeline wall. See, e.g., U.S. Pat. No. 5,751,144 to Weischedel ("Weischedel"). Such methods generate circumferential currents that are best employed when attempting to detect axial cracks. As described in Weischedel, one of the "necessary conditions" for reliable detection is the induction of "substantial eddy currents so that eddy current changes representative of structural faults can be readily detected." To properly induce such eddy currents, the inspection apparatus must first include a small, relative to the two main poles, "auxiliary pole" which "has the same magnetic poling as one of the primary poles" and the apparatus must be moving at a rate in excess of, generally, about four miles per hour ("mph") relative to the pipeline wall to generate measurable and reliable eddy current signals. In addition, inspection apparatus which induce and rely upon eddy currents must necessarily induce only magnetically saturated states to reduce permeability and allow the eddy currents to penetrate the entire pipeline wall thickness. Sensors are placed to detect maximum eddy current. In contrast, MFL-based apparatus rely upon MFL for detecting changes in the magnetic field associated with corrosion and mechanical damage. Eddy currents, which can interfere with the MFL signals, are minimized by selecting a suitable velocity for the apparatus and by positioning sensors where any spurious eddy currents are at a minimum and the magnetic field is most constant.

Each implementation of MFL technology typically focuses on a subset of pipeline wall anomalies that affect pipeline integrity. And, there are varying levels of success, or sensitivity, for each implementation and not all implementations will provide sufficient information for detailed defect assessments.

MFL-based apparatus for detecting corrosion commonly use high magnetic fields to saturate the pipeline material. Such high magnetic field-based apparatus help suppress noise due to local stress variations and changes in the microstructure of the metal. At metal-loss defects, such as those caused by corrosion, an increased amount of magnetic flux attempts to flow through the remaining material, but some flux leaks from the pipeline wall. In addition, a second phenomenon causes even more flux to leak. In magnetically saturated materials, an increase in flux causes the flux-carrying capability (permeability) to decrease. This double effect of increased flux and decreased flux-carrying capacity results in significant flux leakage at such defects.

Stress and material variations can also change the flux-carrying capacity of magnetic materials such as metal pipe. A local decrease in flux-carrying capacity causes leakage similar to that resulting from metal-loss defects. A local increase in flux-carrying capacity causes a decrease in flux leakage relative to the nominal, magnetic field level. For example, for tensile stresses, the overall flux levels in the pipeline increase. For compressive stresses, such as cold-worked areas, the flux levels decrease. It is known, for example, that such flux density variations between tensile stresses and compressive stresses are small for magnetic field levels greater that about 80 Oersted and particularly for magnetic field levels greater than about 120 Oersted. As will be appreciated by one skilled in the art, however, these values may vary by up to 20 percent with pipeline wall chemical composition, grain structure, and fabrication methods. As discussed above, most MFL-based apparatus for corrosion are designed to operate above these levels to reduce stress noise. To detect stress changes in the pipeline wall, however, the magnetic field must be at lower, unsaturated levels, typically about between 50 and 70 Oersted. Unfortunately, field levels in this range can produce results that are difficult to interpret because they can be affected by corrosion, stresses, and changes in material composition. For example, stress damage is often accompanied by metal loss due to corrosion. While current commercially-available low field strength MFL-based apparatus can be used to detect stresses and material variations using fields in the range of about 50 to 70 Oersted, noise and signal processing and interpretation to properly detect anomalies is difficult.

Thus, two magnetic field levels can improve the detection and assessment of pipeline anomalies. The high magnetic field employed in most inspection apparatus detects and sizes metal loss such as corrosion. A low magnetic field must also be applied to detect the metallurgical changes caused by mechanical damage (e.g., from excavation equipment). It is known, therefore, to utilize an approach using more than one apparatus sent separately through the pipeline. This approach, however, is expensive and disruptive to the operation of the pipeline. A single apparatus having two separate sets of magnetizers, while a technically feasible way to apply dual magnetization technology, results in an increase in the size of the apparatus to unacceptable lengths. In addition, when the two magnetizers are placed in close proximity to one another, a magnetic interaction occurs which distorts the constant magnetizing fluxes. In this case, the lower field slightly increases the high field, but, more importantly, the high field distorts the zone of constant magnetization for low magnetization levels. Furthermore, this effect is more pronounced at higher apparatus velocities.

There is, therefore, a need for a single MFL-based apparatus and method which is capable of detecting metal loss such as corrosion as well as stresses such as those caused by mechanical damage.

BRIEF DESCRIPTION OF THE INVENTION

An improved design for an MFL-based pipeline inspection apparatus has been developed. Both high and low fields are attained with a three-pole configuration. Preferably, the strongest pole is at the center of the apparatus and tuned, weaker poles at the leading and trailing edges. The weaker poles have the same magnetic polarity and the strong pole at the center has an opposite magnetic polarity. The design may also be implemented with a backing bar that pivots at bends and obstructions and which, when the pivot point is placed at a magnetic null point in the center pole, will not significantly interfere with the magnetic performance of the apparatus.

In one embodiment of the present invention, an apparatus for pipeline integrity monitoring comprises a magnetically permeable backing bar, a first magnet having a relatively moderate magnetizing field strength positioned proximate to a first end of the backing bar, a second magnet having a relatively strong magnetizing field strength positioned proximate to the central portion of the backing bar, and a third magnet having a relatively moderate magnetizing field strength positioned proximate to a second end of the backing bar. Preferably, the polarity of the second magnet is opposite the polarity of the first magnet and the polarity of the third magnet is the same as the polarity of the first magnet.

In a more general embodiment of the present invention, an apparatus for detecting anomalies in a magnetically permeable object comprises a magnetically permeable backing bar and a least three magnets wherein the at least three magnets are positioned to induce a plurality of resultant fields.

In yet another embodiment of the present invention, a method comprises the steps of inserting an apparatus according to the present invention into a pipeline, traversing the apparatus through at least a portion of the pipeline, inducing at least a first resultant field having a strength greater than 120 Oersted, and inducing at least a second resultant field having strength between 40 and 80 Oersted.

DETAILED DESCRIPTION OF THE INVENTION

Figure 1:
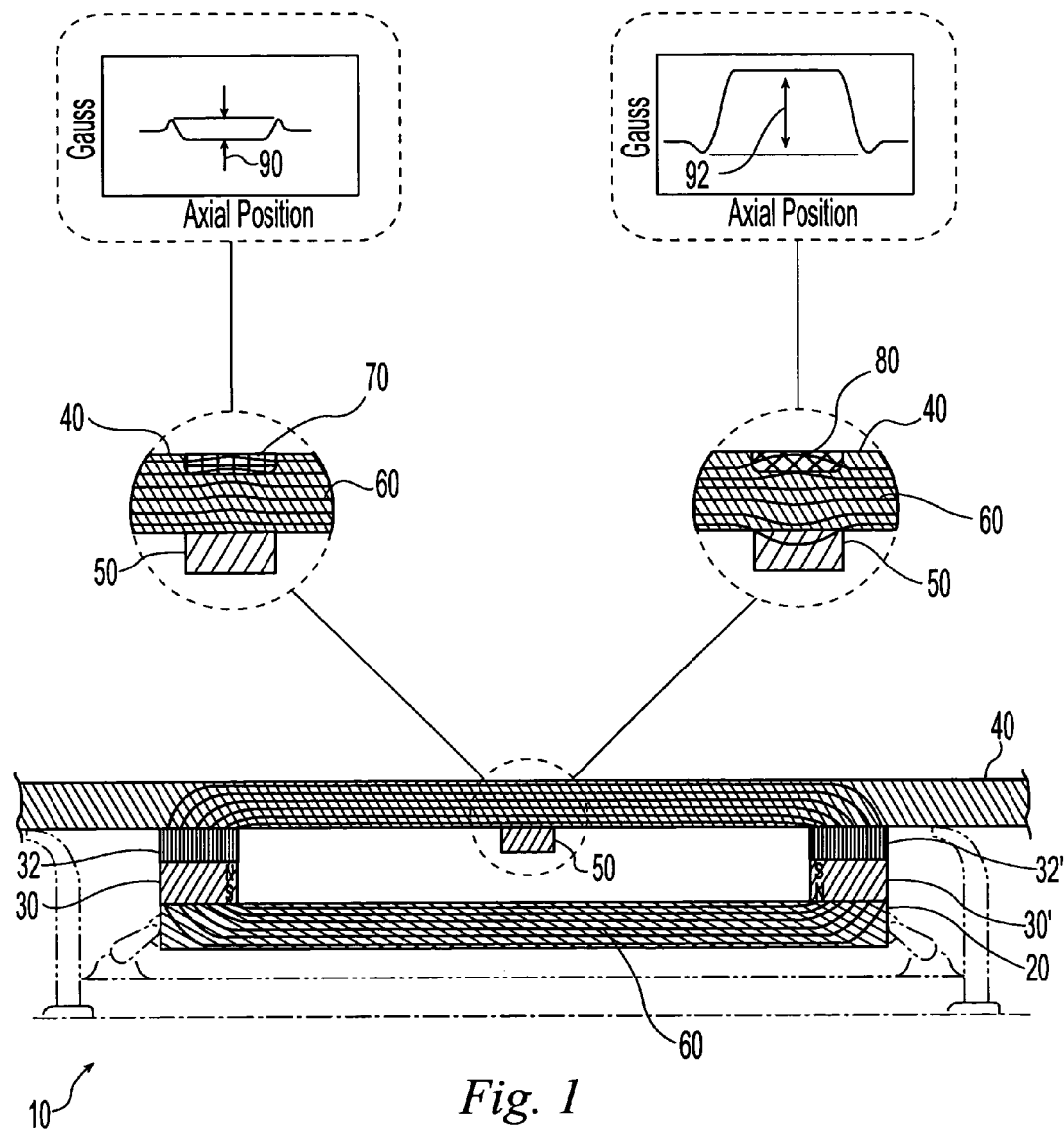
FIG. 1 is a cutaway view of a portion of a conventional two-pole, single-field MFL-based high magnetic field pipeline inspection apparatus showing the effects on magnetic flux caused by a mechanical (stress) defect and a corrosion (metal loss) defect.

Referring now to FIG. 1, a portion of a conventional high-strength, two-pole, single-field MFL-based apparatus 10 is shown which is adapted to sense anomalies in a pipeline wall 40. Included are a first high-strength magnet 30 and a second high-strength magnet 30' in magnetic communication with each other through a backing bar 20. The first high-strength magnet 30 and the second high-strength magnet 30' produce a generally high strength field (e.g., 120 to 200 Oersted) in the pipeline wall 40. Also included are a first means 32 for enabling magnetic communication between the first high-strength magnet 30 and the pipeline wall 40 and a second means 32' for enabling magnetic communication between the second high-strength magnet 30' and the pipeline wall 40. As will be appreciated by one skilled in the art, first means 32 and second means 32', while conventionally wire brush-like elements, may be any equivalent structure which enables a high magnetic flux 60 to flow through the pipeline wall 40 and dynamically maintain magnetic communication between the first high-strength magnet 30, the second high-strength magnet 30', and the pipeline wall 40 as the apparatus 10 travels through along the pipeline wall 40. Other examples include rollers, leaf springs, and a thin friction-reducing coating. A suitable sensor 50 is provided to detect the leakage or other disturbances in the magnetic flux 60 flowing through the pipeline wall 40.

Shown in graphical inset in FIG. 1 is an area of stress 70, caused, for example, by mechanical damage. As will be appreciated by one skilled in the art, the magnetic flux 60 will tend be distorted toward the area of stress 70. Such distortion may then be detected by the sensor 50. Shown in related graphical inset in FIG. 1 is a typical plot of Gauss versus Axial Position for an area of stress 70 as detected by the sensor 50. As will be appreciated by one skilled in the art, the amplitude 90 of such distortion is small (e.g., generally on the order of about 10 Gauss) and, thus, difficult for the sensor 50 to detect and distinguish from background noise.

Also shown in graphical inset in FIG. 1 is an area of metal loss 80. As will be appreciated by one skilled in the art, the reduced volume of metal caused by the area of metal loss 80 will produce a distortion and leakage of the magnetic flux 60 which may then be detected by the sensor 50. Shown in related graphical inset in FIG. 1 is a typical plot of Gauss versus Axial Position for an area of metal loss 80 as detected by the sensor 50. As will be appreciated by one skilled in the art, the amplitude 92 of such leakage is relatively large (e.g., generally on the order of 100 Gauss or more). The amplitude 92 produced by an area of metal loss 80 is, therefore, more readily distinguished from background noise than the amplitude 90 produced by an area of stress 70.

Figure 2:
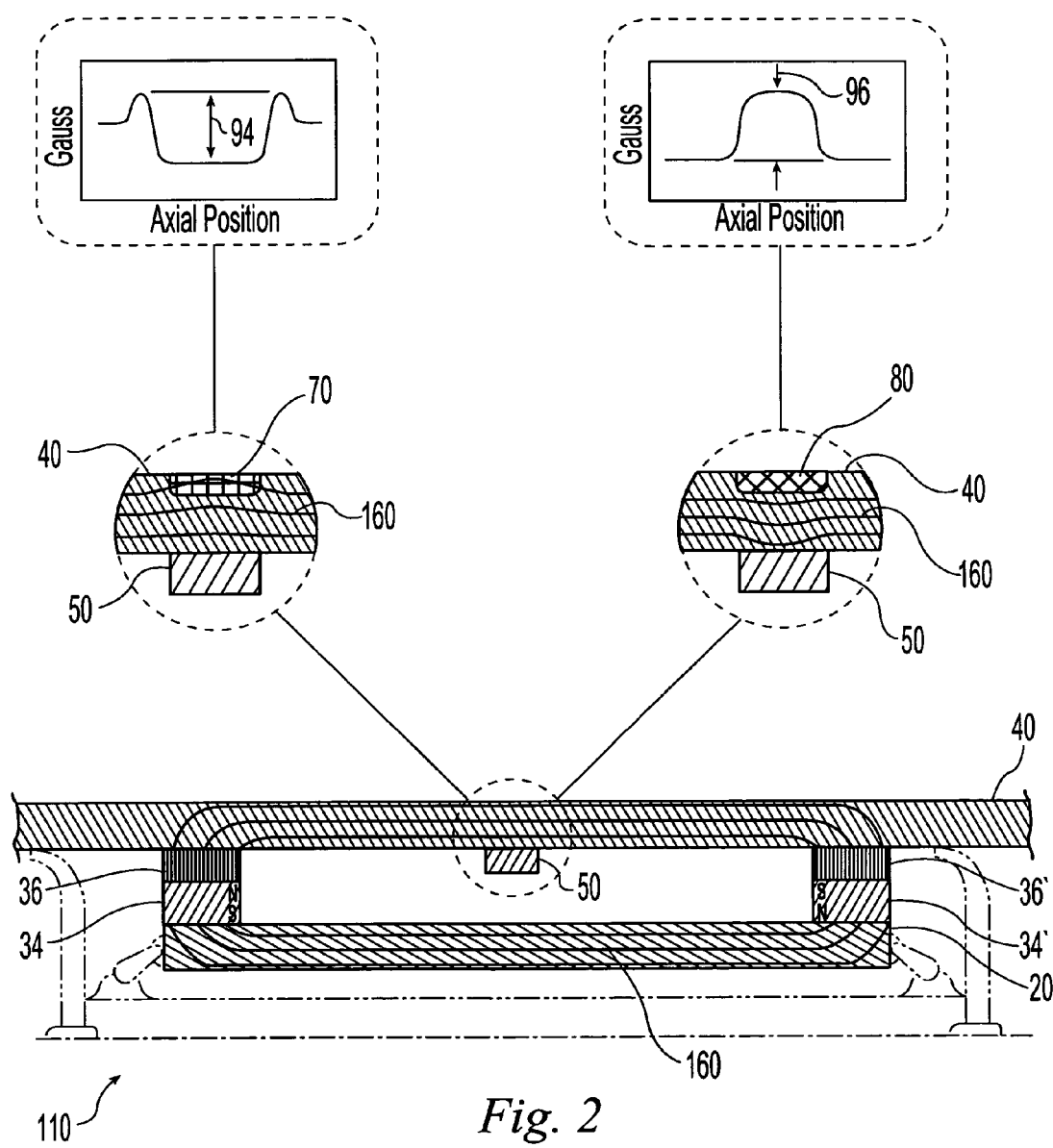
FIG. 2 is a cutaway view of a portion of a conventional two-pole, single-field MFL-based low magnetic field pipeline inspection apparatus showing the effects on magnetic flux caused by a mechanical (stress) defect and a corrosion (metal loss) defect.

Referring next to FIG. 2, a portion of a conventional low-strength, two-pole, single-field MFL-based apparatus 110 is shown which is adapted to sense anomalies in a pipeline wall 40. Included are a first low-strength magnet 34 and a second low-strength magnet 34' in magnetic communication with each other through a backing bar 20. The first low-strength magnet 34 and the second low-strength magnet 34' are sized to produce a resultant field strength in the pipeline wall 40 of 40 to 80 Oersted. Also included are a first means 36 for enabling magnetic communication between the first low-strength magnet 34 and the pipeline wall 40 and a second means 36' for enabling magnetic communication between the second low-strength magnet 34' and the pipeline wall 40. Again, as will be appreciated by one skilled in the art, first means 36 and second means 36', while conventionally wire brush-like elements, may be any equivalent structure which enables the magnetic flux 160 to flow through the pipeline wall 40 and dynamically maintain magnetic communication between the first low-strength magnet 34, the second low-strength magnet 34', and the pipeline wall 40 as the apparatus 110 travels through along the pipeline wall 40. A sensor 50 is provided to detect the leakage or other disturbances in the magnetic flux 160 flowing through the pipeline wall 40.

Shown in graphical inset in FIG. 2 is an area of stress 70 caused, for example, by mechanical damage. As will be appreciated by one skilled in the art, the magnetic flux 160 will be distorted toward the area of stress 70. Such distortion may then be detected by the sensor 50. Shown in related graphical inset in FIG. 2 is a typical plot of Gauss versus Axial Position for an area of stress 70 as detected by sensor 50. As will be appreciated by one skilled in the art, the amplitude 94 of such distortion (e.g., generally on the order of about 30 Gauss) is somewhat larger than the amplitude 90 in the high-field case shown in FIG. 1 and, thus, more easily detected by the sensor 50 and distinguished from background noise.

Also shown in graphical inset in FIG. 2 is an area of metal loss 80. As will be appreciated by one skilled in the art, the reduced volume of metal caused by the area of metal loss 80 will produce a distortion and leakage of the magnetic flux 160 which may then be detected by the sensor 50. Shown in related graphical inset in FIG. 2 is a typical plot of Gauss versus Axial Position for an area of metal loss 80 as detected by the sensor 50. As will be appreciated by one skilled in the art, the amplitude 96 of such leakage is relatively equal to that produced by the stress 70 (e.g., generally on the order of about 30 Gauss) but of opposite direction.

Figure 3:
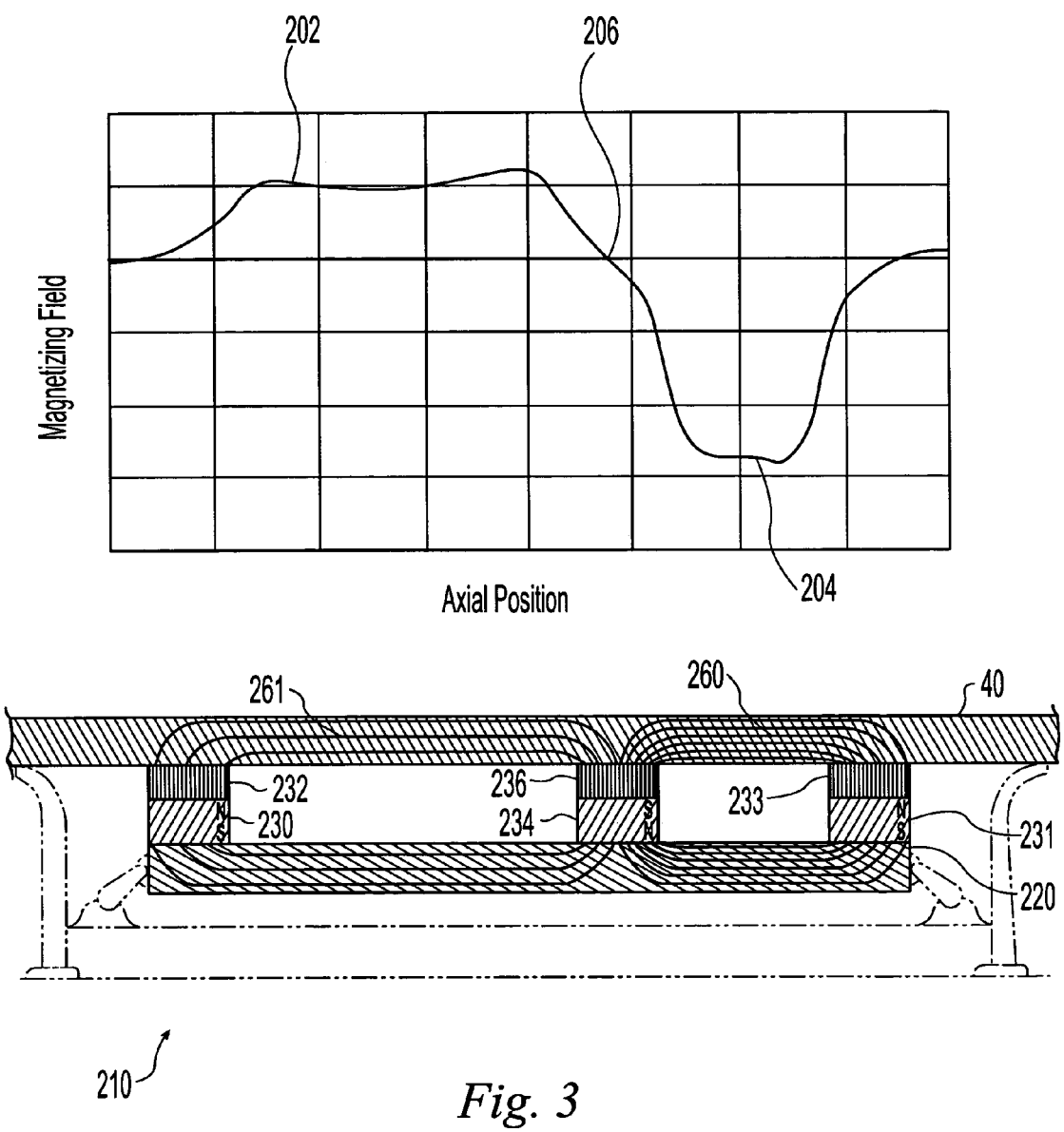
FIG. 3 is a cutaway view of a portion of a three-pole, two-field MFL-based pipeline inspection apparatus according to the present invention showing a static baseline flux pattern.

FIG. 3 illustrates a portion of a multi-strength, three-pole, two-field MFL-based apparatus 210 according to the present invention. The portion of the apparatus 210 comprises a first magnet 230, a second magnet 234, and a third magnet 231 in magnetic communication with each other through a backing bar 220. The first magnet 230 is preferably of generally relatively low strength, the second magnet 234 is preferably of generally relatively high strength, and the third magnet 231 is preferably of generally relatively moderate strength compared with the first magnet 230 and the second magnet 231. Both the absolute and relative strengths of the three magnets 230, 234, 231 may vary to accommodate differing pipeline wall 40 materials and thicknesses, the type of anomalies detected, and the velocity of the apparatus 210 along the pipeline wall 40. The strength of the various magnets 230, 234, 231 is selected to produce a relatively high resultant field 260 of greater that 120 Oersted and a relatively low resultant field 261 of between 40 and 80 Oersted. Applicants have found, however, that a preferred resultant field is effected with the second (strongest) magnet 234 being positioned between the first magnet 230 of generally low strength and the third magnet 231 of generally relatively moderate strength. Furthermore, and importantly, each of the first magnet 230, the second magnet 234, and the third magnet 231 may comprise a plurality of magnets together to produce the desired strength. As shown, the first magnet 230 and the second magnet 231 are of like polarity while the third magnet 234 is of opposite polarity. Also included are a first means 232, a second means 236, and a third means 233 for enabling magnetic communication between the first magnet 230, the second magnet 234, and the third magnet 231, respectively, and the pipeline wall 40. As with FIGS. 1 and 2, appropriate sensors (not shown in FIG. 3) are included to detect the flux leakage.

Also shown in FIG. 3 is a finite-element analysis (FEA) representation of the nominal field strength in the pipeline wall 40. A low resultant field is indicated by a curve 202 having a relatively low amplitude but having a relatively longer axial length. A high resultant field is indicated by a curve 204 having a relatively high amplitude and a relatively shorter axial length. As will be appreciated by one skilled in the art, a relatively long section of a relatively flat field is desirable. This is particularly true with the low field strength curve 202 where velocity effects can cause distortion and interference. Also shown in FIG. 3 is an FEA representation of a null point 206 where the field strength crosses the zero value on the ordinate showing magnetizing field.

Figure 4:
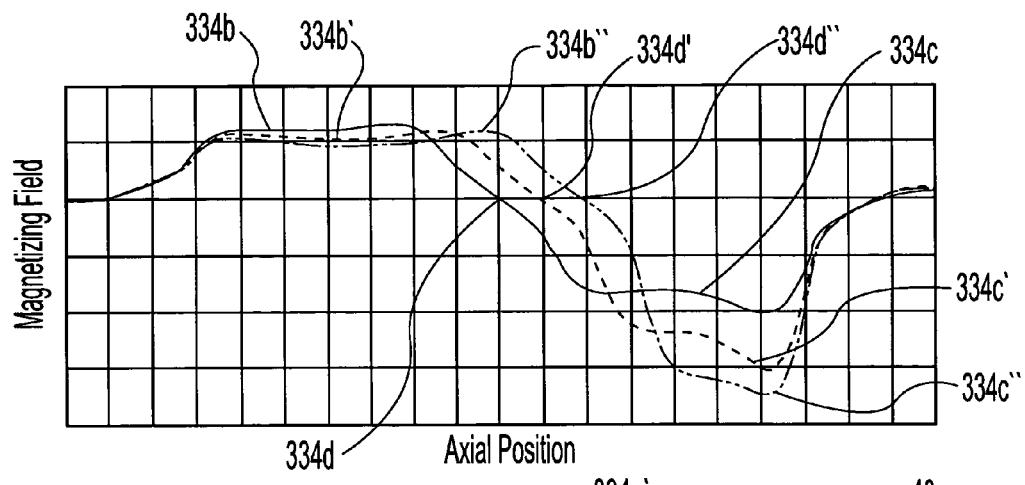
FIG. 4 is a cutaway view of a portion of a three-pole, two-field MFL-based pipeline inspection apparatus according to the present invention showing the effects of magnet configuration on a static baseline flux pattern.
Figure 4:
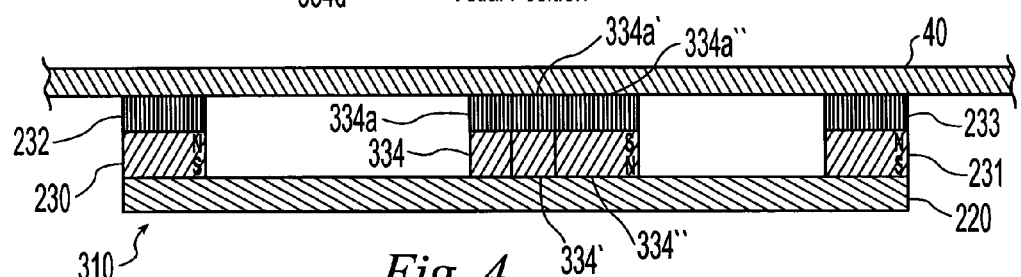

FIG. 4 illustrates a portion of a multi-strength, three-pole, two-field MFL-based apparatus 310 according to the present invention showing the effects of the position of a second magnet 334, 334', 334" on magnetization levels. As the FEA representation of FIG. 4 shows, the greater the distance between a first magnet 230 and the second magnet 334, 334', 334" the longer (and lower amplitude) a resultant field 334b, 334b', 334b", respectively. Conversely, the smaller the distance between the second magnet 334, 334', 334" and a third magnet 231, the shorter (and higher amplitude) the resultant field 334c, 334c', 334c", respectively. Also shown in FIG. 4 is an FEA representation of a first null point 334d, a second null point 334d', and a third null point 334d", corresponding to the position of the second magnet 334, 334', 334", respectively. Thus, the null point 334d, 334d', 334d" is determined primarily by the position of the second magnet 334, 334', 334", respectively, the ratio of the strengths of the high resultant field 334c, 334c', 334c", respectively, and low resultant field 334b, 334b', 334b", respectively, and the inspection velocity. (The latter effect causes the null point (e.g., 334d) to shift upstream and is discussed below.)

Figure 5:
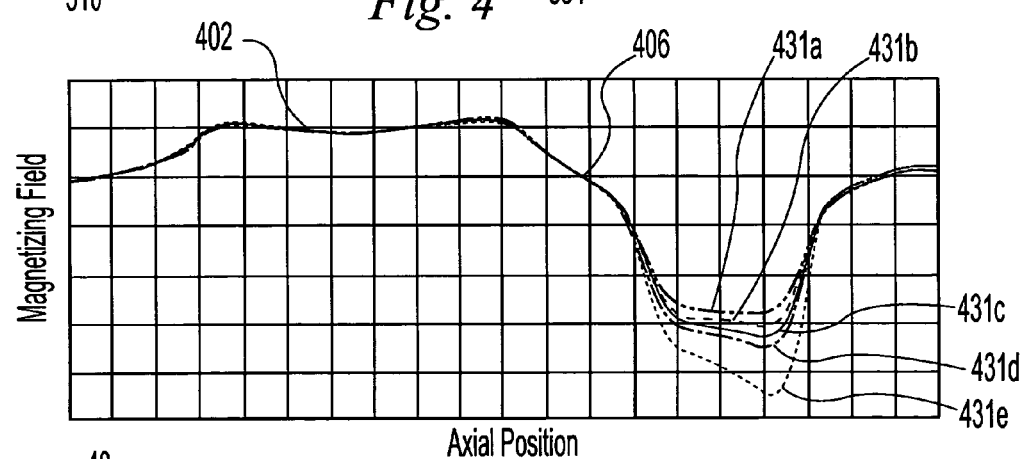
FIG. 5 is a cutaway view of a portion of a three-pole, two-field MFL-based pipeline inspection apparatus according to the present invention showing the effects of varying magnetic configuration on a static baseline flux pattern.
Figure 5:
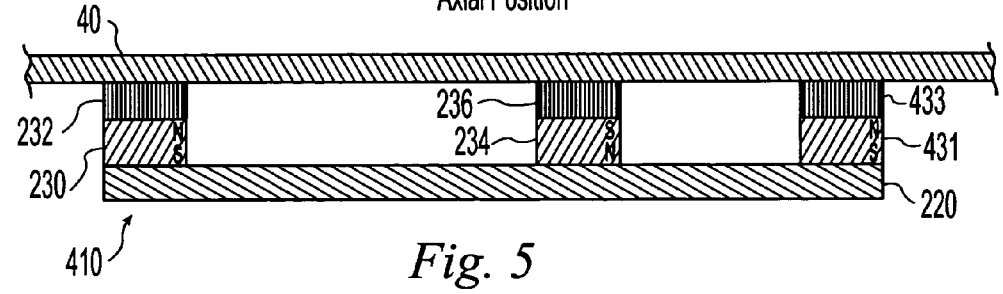

FIG. 5 illustrates a portion of a multi-strength, three-pole, two-field MFL-based apparatus 410 according to the present invention showing the effects of the strength of a third magnet 431 on magnetization levels. As the FEA representation of FIG. 5 shows, the greater the strength of the third magnet 431, the greater the amplitude of the high-strength resultant field. Curves 431a, 431b, 431c, 431d, and 431e of the FEA representation represent a third magnet 431 strength of 28, 30, 32, 35, and 42 megaGauss-Oersted, respectively. While the low-field curve 402 and the null point 406 show no appreciable change, the high-field amplitude increases and the shape becomes more distorted as the strength of the third magnet 431 increases.

Figure 6:
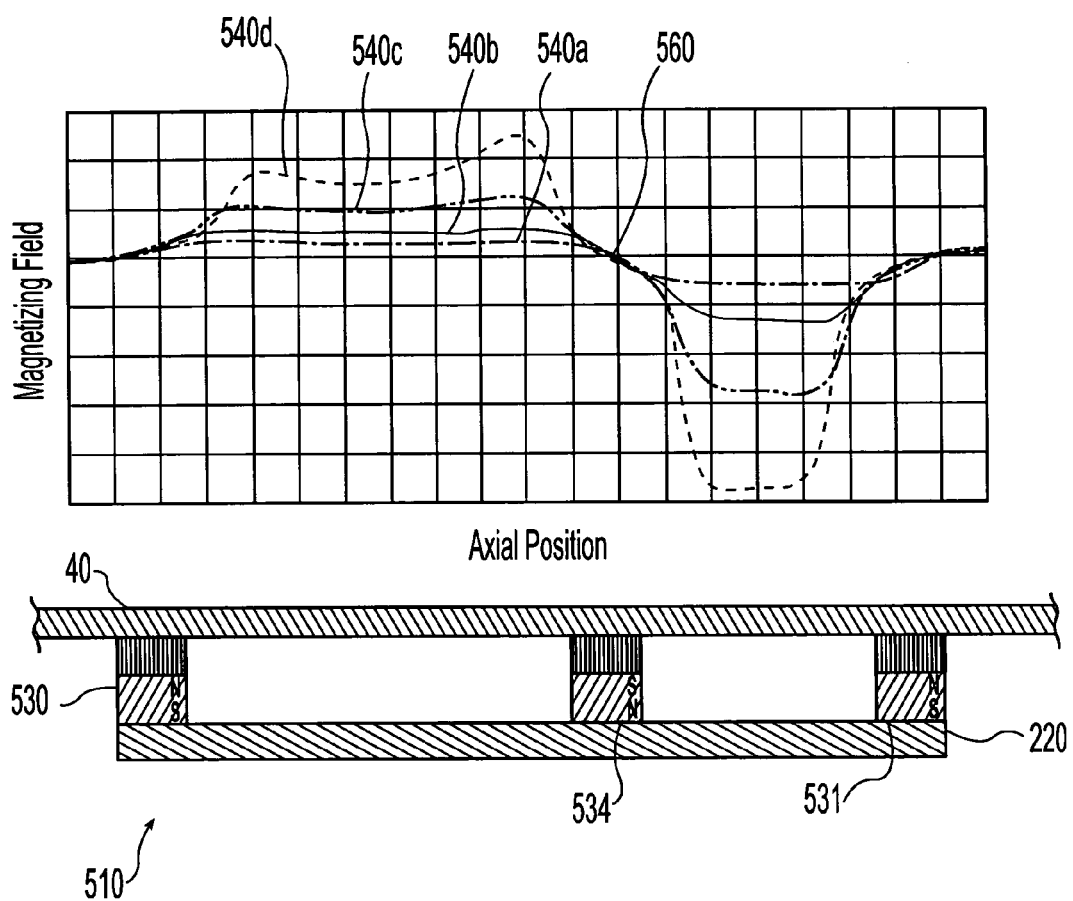
FIG. 6 is a cutaway view of a portion of a three-pole, two-field MFL-based pipeline inspection apparatus according to the present invention showing the effects of varying magnetic strength on a static baseline flux pattern.

FIG. 6 illustrates a portion of a multi-strength, three-pole, two-field MFL-based apparatus 510 according to the present invention showing the effects of varying the strength of each magnet simultaneously. As the FEA representation of FIG. 6 shows, the greater the strengths of the magnets 530, 534, 531, the greater the amplitude of both the low-strength and the high-strength resultant fields. Curves 540a, 540b, 540c, 540d of the FEA representation represent magnet strengths that produce a range of resultant field strengths in the pipeline wall 40. Again, while the null point 560 does not change significantly, the amplitude increases and the shape becomes more distorted as the strength of the magnets 530, 534, 531 increases.

Figure 7:
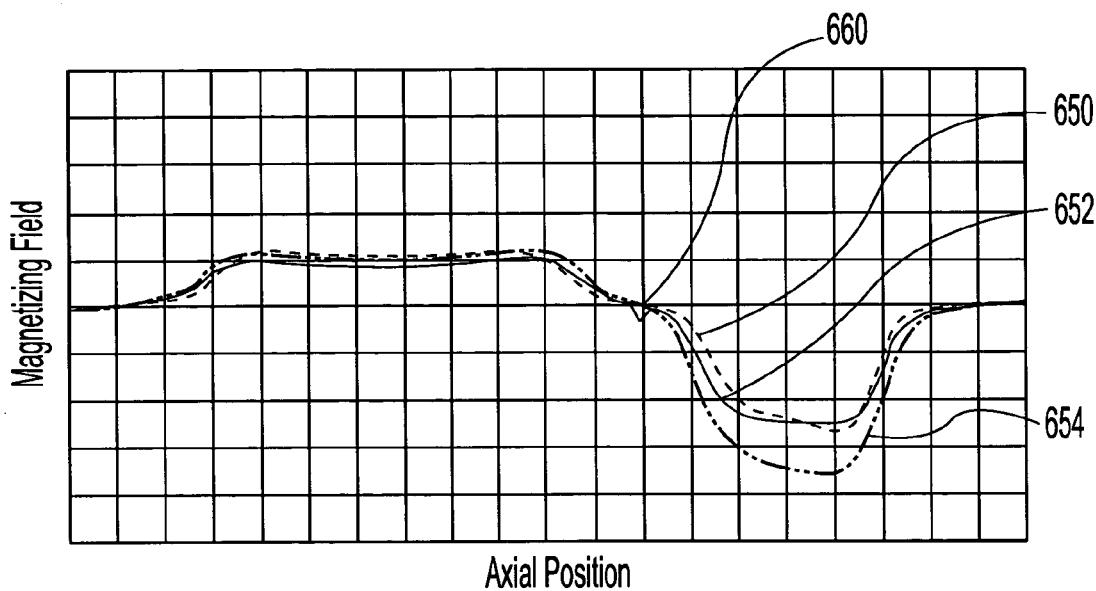
FIG. 7 is a cutaway view of a portion of a three-pole, two-field MFL-based pipeline inspection apparatus according to the present invention showing the effects of varying pipeline material magnetic properties on a static baseline flux pattern.

FIG. 7 illustrates a portion of a multi-strength, three-pole, two-field MFL-based apparatus (FIG. 8, 610) according to the present invention showing the effects on varying pipeline wall 40 magnetic properties (B-H Curve). As the FEA representation of FIG. 7 shows, as the B-H Curve becomes more pronounced (greater "knee"), there is little change to the low-strength resultant field, somewhat more pronounced change to the high-strength resultant field 650, 652, 654 and the null point 660 does appear to not change.

Figure 8:
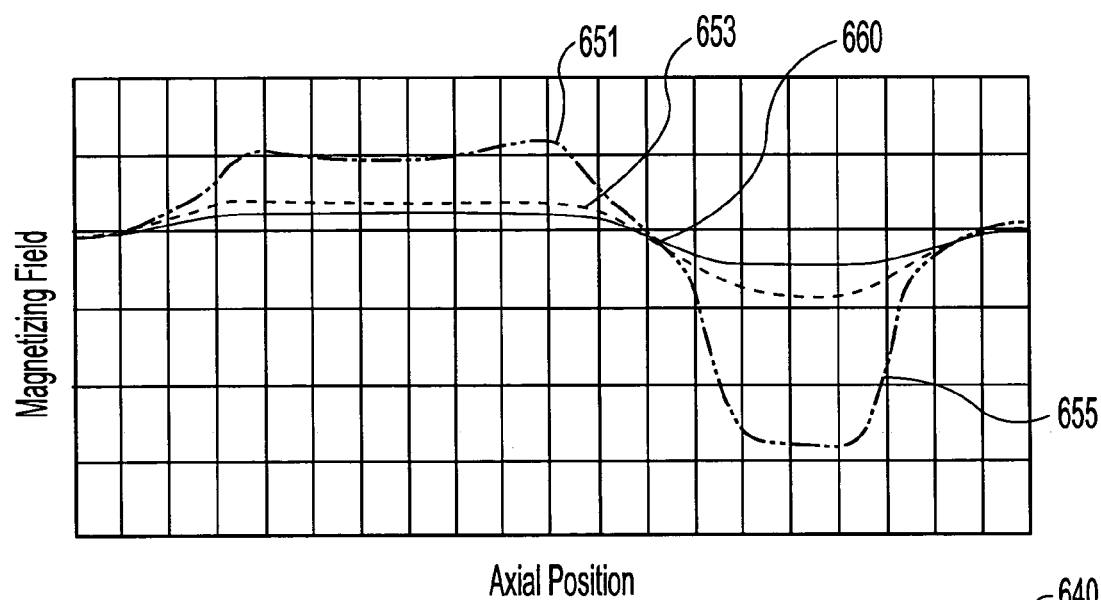
FIG. 8 is a cutaway view of a portion of a three-pole, two-field MFL-based pipeline inspection apparatus according to the present invention showing the effects of varying pipeline wall thickness on a static baseline flux pattern.
Figure 8:
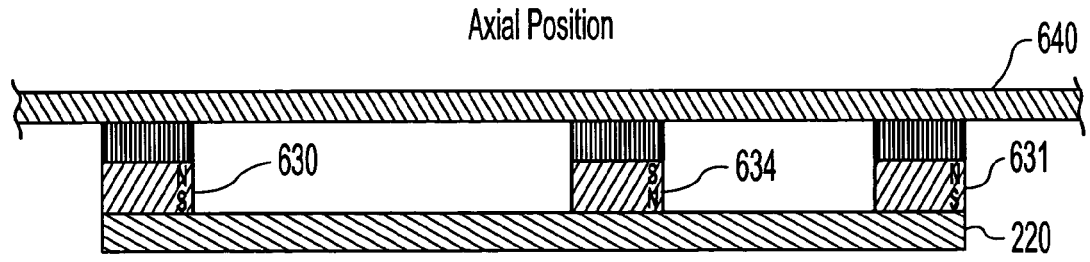

FIG. 8 illustrates a portion of a multi-strength, three-pole, two field MFL-based apparatus 610 according to the present invention showing the effects of the thickness of the pipeline wall 40. As the FEA representation of FIG. 8 shows, wall thickness can be a significant variable. In the FEA graphic shown, a wall thickness of 0.30 inches produces curve 651, a wall thickness of 0.50 inches produces curve 653, and a wall thickness of 0.75 inches produces curve 655. The magnet configuration was held constant. Various combinations of magnet strength and pole lengths can be used to induce an optimum field level for pipe up to about 0.5 inches thick. While the signal processing technique to detect cold work-material works best when the high resultant field is above 150 Oersted, reasonable results may be obtained if this field exceeds 110 Oersted. Again, the null point 660 does not appear to change.

The optimum speed for operation of most MFL-based in-line inspection apparatus is between one and six miles per hour. The lower value is constrained by inspection time (e.g., battery life) and, in some instances, sensor type. The upper end value is determined by the velocity effect of the MFL magnetizer. At higher speeds, MFL signals become distorted by eddy currents generated in the pipeline wall 40. The speed at which the distortion becomes significant depends to a very great extent upon resultant field level, the thickness of the pipeline wall 40, and magnetic pole spacing. For a static or very slow-moving magnetizer, the resultant field is uniform across the thickness of the pipeline wall 40. As the velocity increases, however, changes in the distribution of the resultant field occur as illustrated in FIGS. 9a–9d.

Figure 9B:
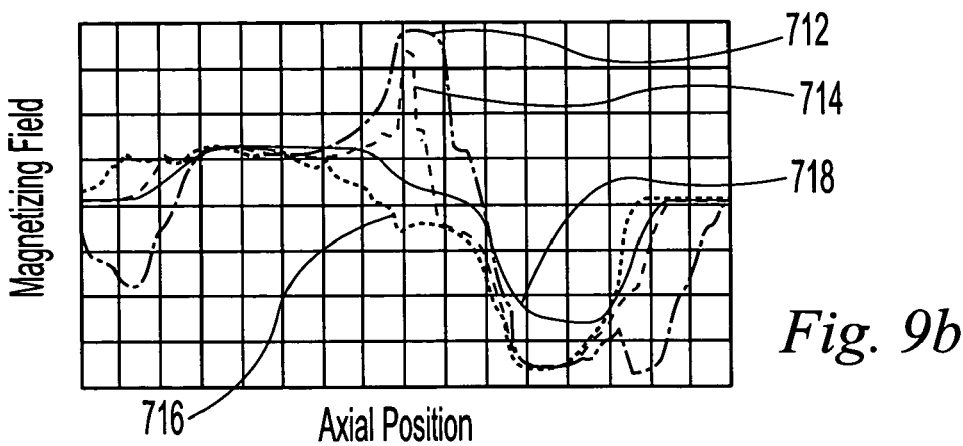
FIG. 9 is a cutaway view of a portion of a three-pole, two-field MFL-based pipeline inspection apparatus according to the present invention showing the effects of varying apparatus velocity on the dynamic flux pattern for various pipeline wall thicknesses.

FIG. 9b is an FEA representation of the effect of a 30-inch long magnetizer (backing bar 220) according to the present invention traveling at 5.0 mph through a pipeline having a wall thickness of 0.3 inches. A zero velocity (static) curve 718 is shown as a reference. As shown in FIG. 9b, the resultant field near the inner wall (0.01 inches from the inner wall) (curve 712) increases and near the outer wall (0.01 inches from the outer wall) (curve 716) decreases. Also, the fields at the inner surface increase most at the center pole. In the high magnetization zone, the field levels are initially decreased and then increased. In the low magnetization zone, the field is decreased at the leading edge, but attains a more-desirable level approximately midway between the poles.

Figure 9C:
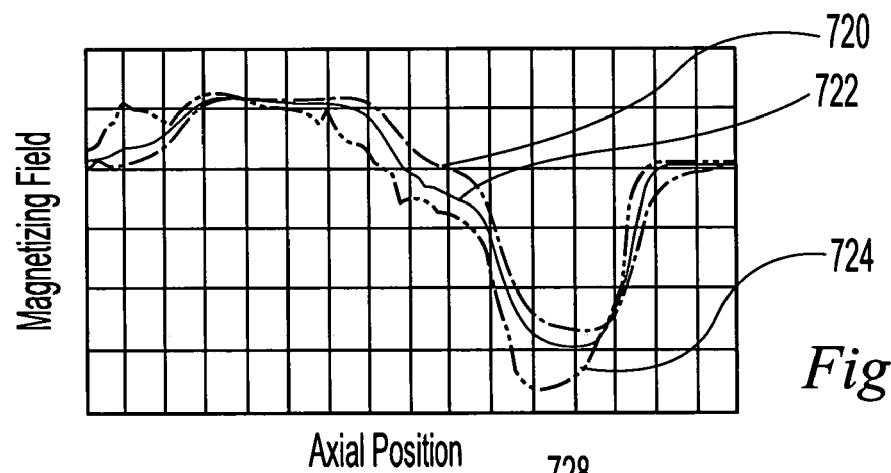
Figure 9D:
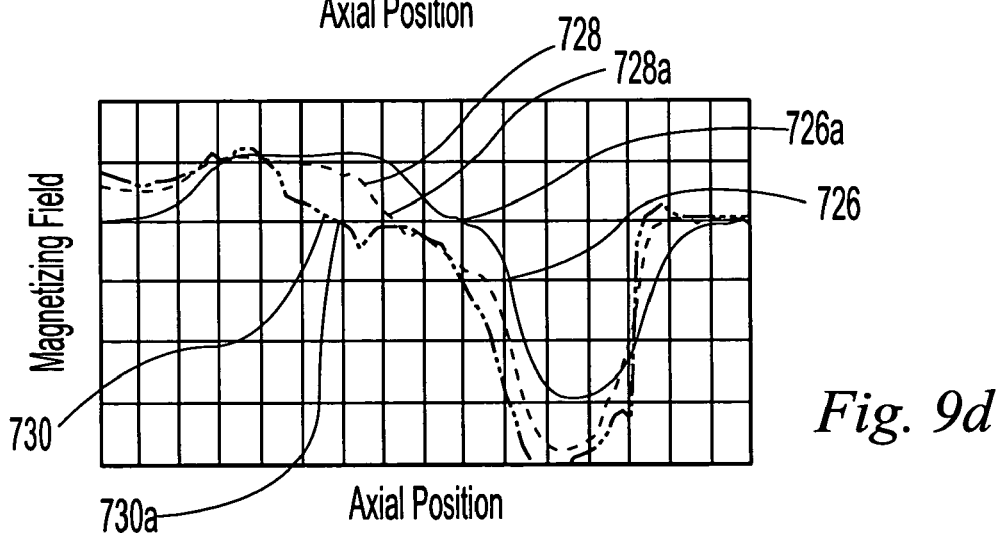
Figure 9A:
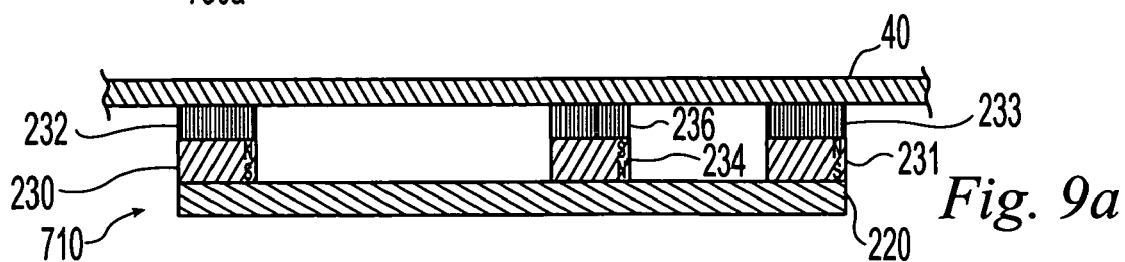

Inspection for mechanical damage is focused on the outer surface. FIG. 9c is an FEA representation showing that the onset of velocity effects is not immediate. The configuration shown is for a 30-inch long magnetizer (backing bar 220) and a pipeline wall 40 thickness of 0.3 inches with a typical magnetic permeability. At 2.5 mph, the velocity effect is minimal (curve 722). At 5.0 mph, there is still a relatively large zone of nearly constant magnetization level (curve 724) for sensor placement. (For comparison, curve 720 shows a static condition. As illustrated in FIG. 9d, however, while still acceptable, the inspection of a pipeline wall 40 with a thickness of 0.5 inches shows significantly more velocity effects. Curve 726 shows a static condition, curve 728 shows the effects at 2.5 mph, and curve 730 shows the effects at 5.0 mph. Note, too, at higher velocities, the null point 726a, 728a, 730a shifts upstream.

Figure 10:
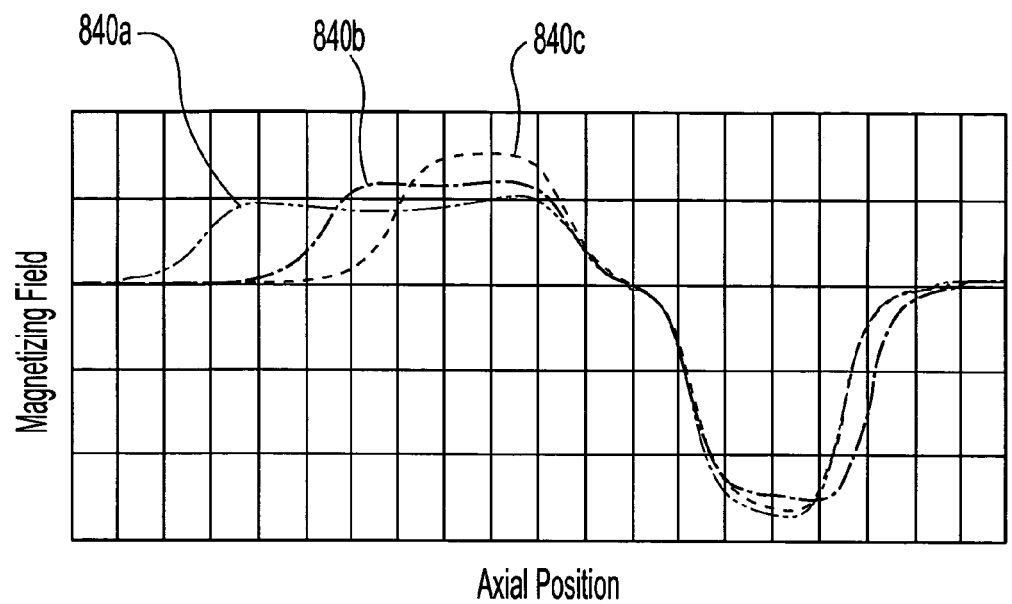
FIG. 10 is a cutaway view of a portion of a three-pole, two-field MFL-based pipeline inspection apparatus according to the present invention showing the effects of varying apparatus length on the static baseline flux pattern.
Figure 10:
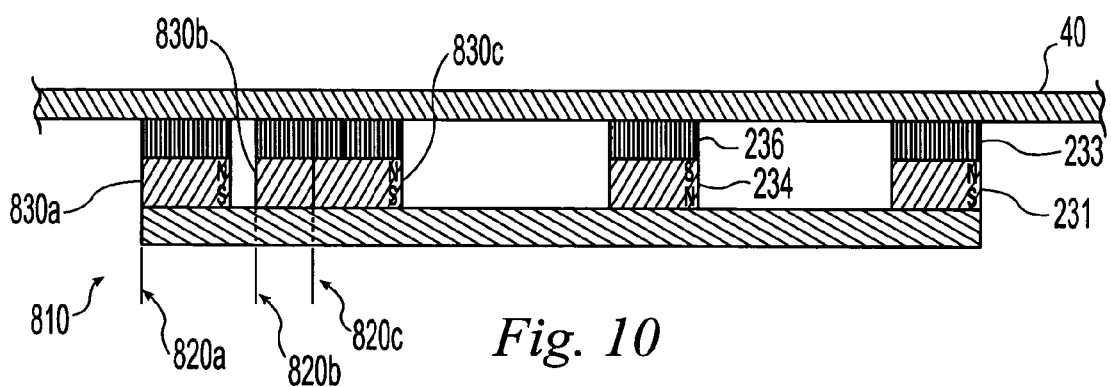

To increase the size of the zones of nearly constant magnetization level, a longer magnetizer would be required with appropriate increases in magnet strength. As shown in FIG. 10, a comparatively longer apparatus 810 provides a significantly longer zone of constant magnetization. Velocity will also have less of an effect. The effects of length 820a (e.g., 36 inches) is shown in the FEA graphic as curve 840a, the effects of length 820b (e.g., 30 inches) as curve 840b, and the effects of length 820c (e.g., 27 inches) as curve 840c.

A longer apparatus 810, however, presents its own problems since bends and other pipeline features limit the length of the apparatus 810.

Figure 11A:
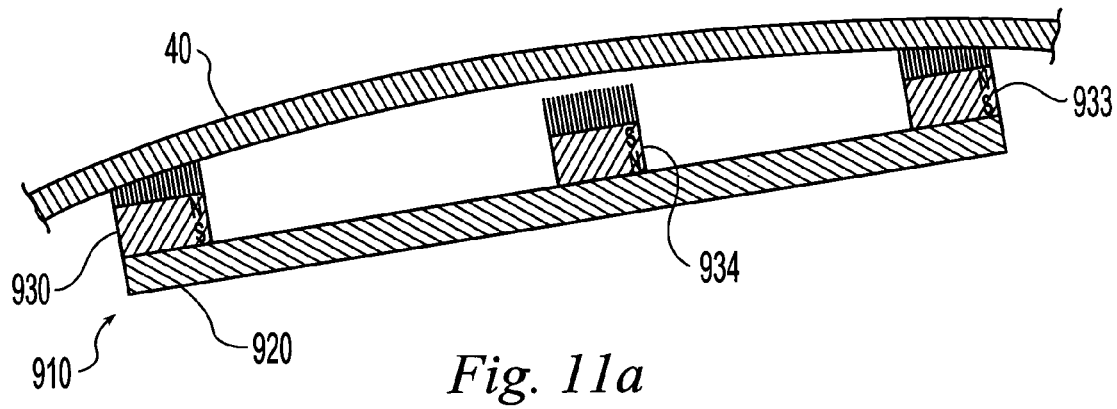
FIG. 11 is a cutaway view of a portion of a three-pole, two-field MFL-based pipeline inspection apparatus showing the effects of encountering a bend in the pipeline.
Figure 11B:
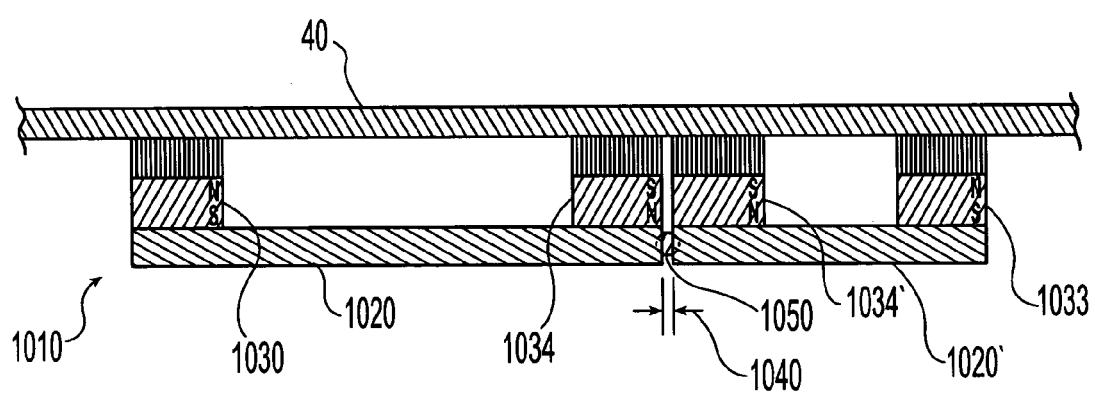
Figure 11C:
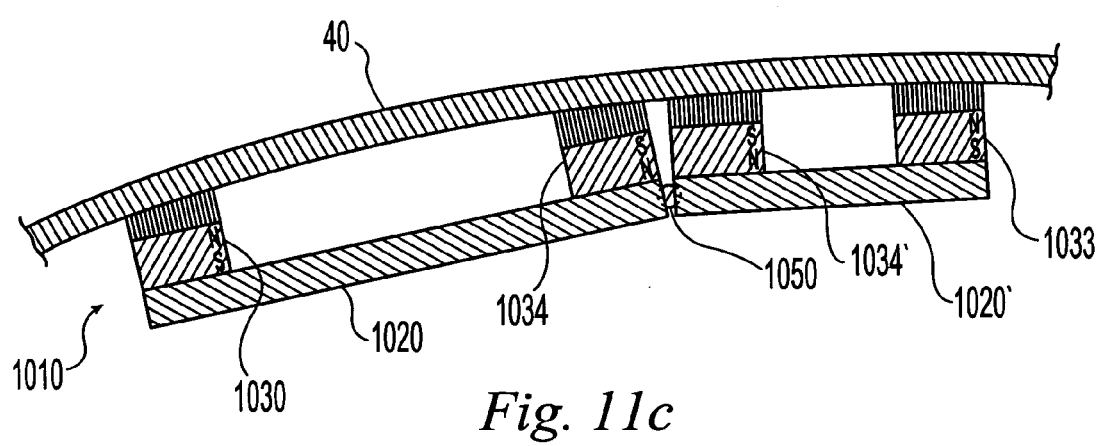

Turning now to FIG. 11*a*, a longer apparatus 910 with a proportionally longer backing bar 920 may present problems when negotiating a curve in the pipeline wall 40. It has been surprisingly found, however, that the magnetic null point 660 (See, FIG. 8) between the high resultant field and the low resultant field enables the placement of an articulated connection 1050 in the backing bar 1020 thus enabling the inspection apparatus 1010 to pass through bends while minimizing interference with the magnetic field. See, FIGS. 11*b* and 11*c*. As will be appreciated by one skilled in the art, the articulated connection 1050 may be any suitable element which enables radial and circumferential relative movement between the multiple segments of the backing bar 1020. Examples would include, but not be limited to, a complex hinge, a ball-and-socket joint, a universal joint, and a flexible material such as rubber or plastic. Preferably such articulated connection 1050 is magnetic. By properly balancing the relative strengths of the first magnet 1030, the second magnet 1033, and a combination third magnet 1034, 1034', the desired profile for the field strength 202, 204 (e.g., FIG. 3) may be achieved and there will be no significant change in the magnetic performance of the apparatus. In addition, since, as shown in FIGS. 9*c* and 9*d*, the null point shifts upstream, the two-pole combination third magnet 1034, 1034' will be balanced to effect placement of the articulated connection 1050 at the desired dynamic null point (e.g., FIG. 9*d*, 728*a*). Applicants have found that the combination third magnet 1034, 1034' performs like a single magnet whose magnetizing strength is approximately the sum of the combination 1034, 1034'. Thus, first pole 1034 of the combination third magnet may be a multiple of a second pole 1034'. A so-called inter-pole gap 1040 must exist between the first pole 1034 and the second pole 1034'. An inter-pole gap 1040 of zero means that the combination third magnet 1034, 1034' collapses to the case of a one-pole magnet. Depending upon the size and configuration of the backing bars 1020, 1020' and the expected pipeline bend radius of curvature, the inter-pole gap 1040 should be as small is practicable. Preferably, about one inch or less, more preferably about one-half inch or less. This will allow the combination third magnet 1034, 1034' to perform as a single pole magnet while still enabling the apparatus 1010 to negotiate the bends in the pipeline.

Figure 12:
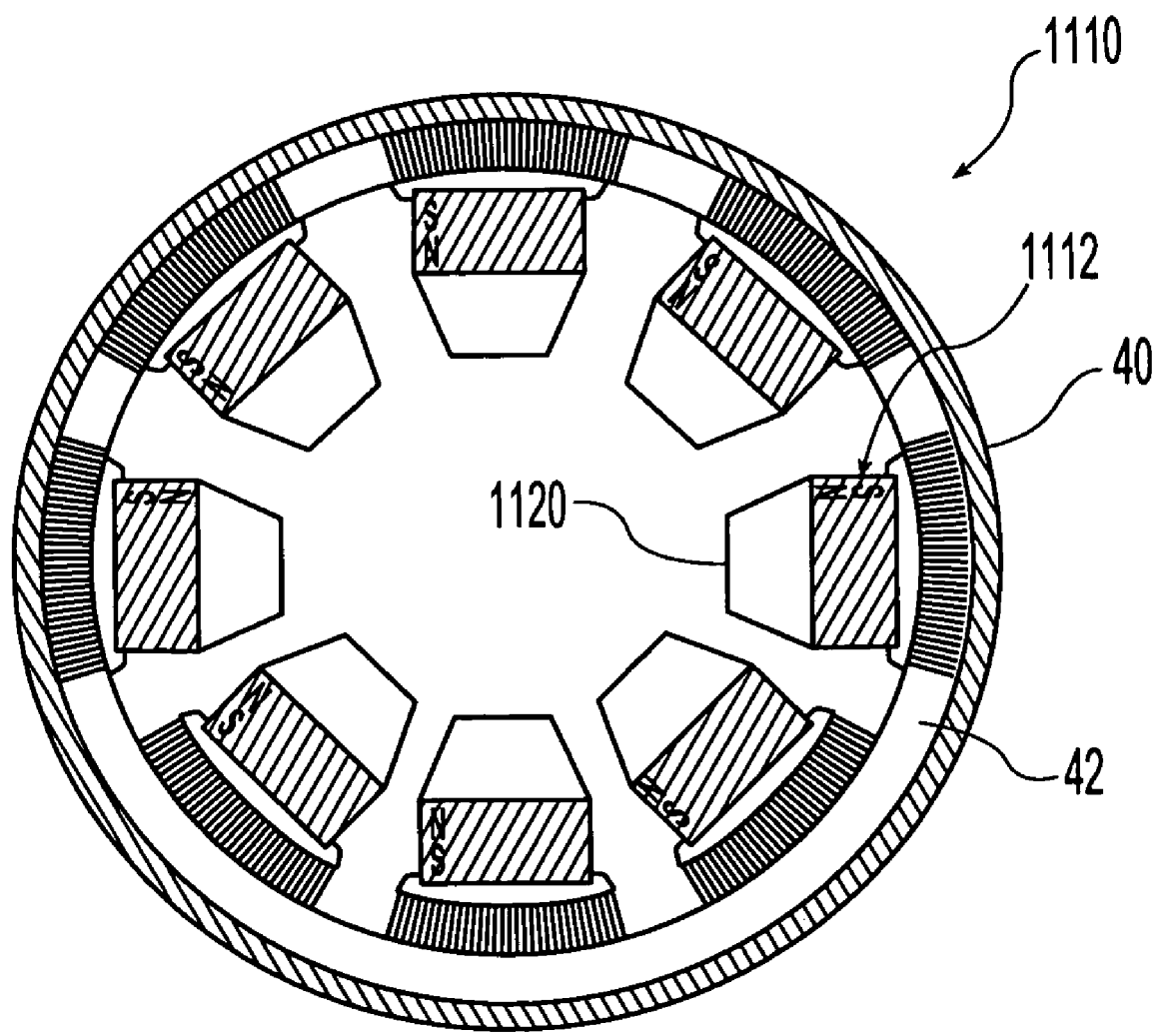
FIG. 12 is a cutaway end view of a pipeline inspection apparatus showing the effects of modifying the profile of the backing bar(s) to provide an improved ability to negotiate bends and improved obstruction clearance.

Even with the articulated connection 1050, the three-pole magnetizer apparatus 1010 may have to be further adapted to pass bends and obstructions while maintaining its magnetic performance. FIG. 12 shows an eight-segment magnetizer apparatus 1110 designed to pass a ten percent obstruction 42. The segments 1112 can be forced together until the widest parts touch. The widest part is typically the backing bar(s) 1120 which may be tapered to facilitate sufficient collapse. Each magnetizer segment 1112 is free to collapse to the center.

Figure 13:
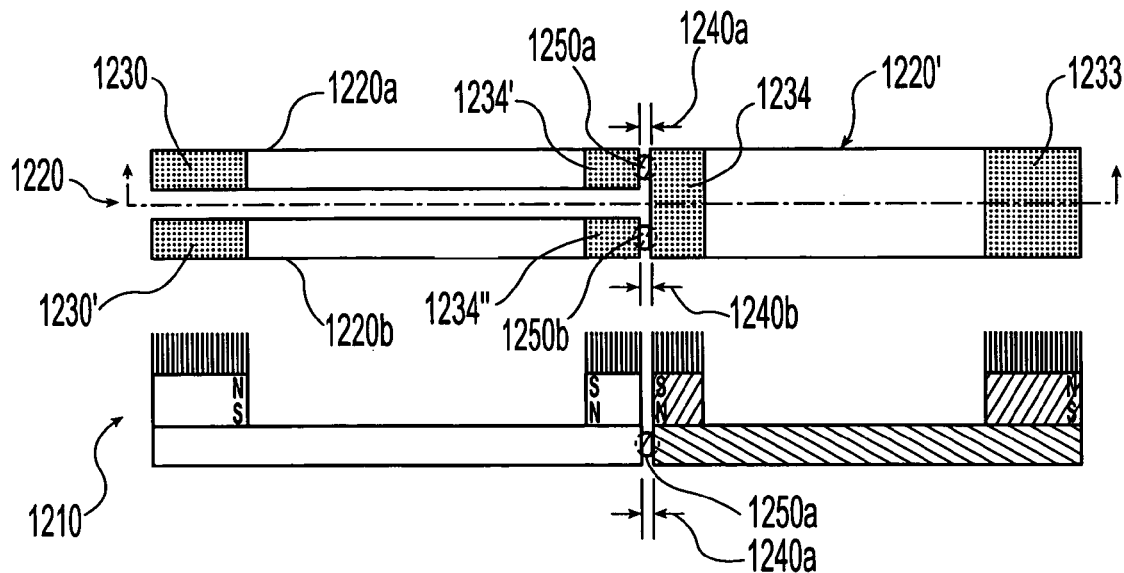
FIG. 13 is a partial cutaway elevation view and a partial plan view of a portion of a three-pole, two-field MFL-based pipeline inspection apparatus showing a split backing bar configuration.
Figure 14:
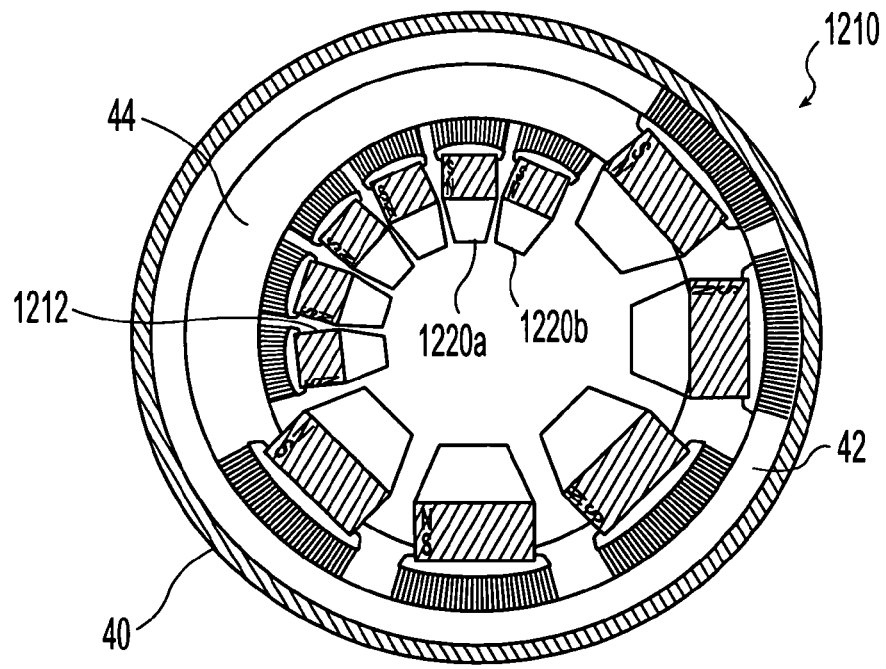
FIG. 14 is a cutaway end view of a pipeline inspection apparatus showing the effects of a split backing bar configuration to provide an improved ability to negotiate bends and improved obstruction clearance.

As shown in FIG. 13, since less flux must be carried by the low-field backing bar 1220, the low-field backing bar 1220 can have a smaller cross-sectional area than the high-field backing bar 1220'. The reduction in cross-sectional area can result from reducing the circumferential extent, the radial extent, or a combination. As shown in FIGS. 13 and 14, the collapse of the segments 1212 of the magnetizer apparatus 1210 can be enhanced in the low-magnetizer side by splitting the low-field backing bar 1220 into a first sub-segment 1220*a* and a second sub-segment 1220*b*, in effect reducing the circumferential extent of the backing bar 1220. As will be appreciated by one skilled in the art, the combined cross-sectional area of the backing bar 1220 should be about twice the cross-sectional area of the pipeline wall 40. However, in the low-field backing bar 1220, the flux density is approximately one-half of the high-field density. Therefore, the cross-section of the low-field backing bar 1220 may be further reduced. Reducing the radial dimension would not provide significant benefit, since this dimension does not constrain the collapse. Keeping the same radial thickness, however, and reducing the circumferential extent will enhance collapse. At the same time, however, the low-field magnetizer must provide a uniform magnetic filed within the pipeline wall. (Not shown in FIG. 13.) This can be accomplished by removing a portion of the middle of the low-field backing bar 1220 to form the first sub-segment 1220*a* and the second sub-segment 1220*b*. This split backing bar 1220*a*, 1220*b*, if designed to carry the flux without saturating, will produce a uniform magnetic field at the desired field level. As shown in FIG. 13, the magnet configuration would include a, for example, moderate-strength magnet 1233, two relatively weaker-strength magnets 1230, 1230', and magnets 1234, 1234', 1234" which combine into a higher-strength magnet. Looking then at FIG. 14, the collapse of the sub-segments 1220*a*, 1220*b* is further enhanced. Now, a tighter bend or an obstruction 44 greater than the ten percent obstruction 42 can be negotiated by the apparatus 1210.

While the present invention has been described in several embodiments, it will be understood that numerous modifications and substitutions may be made without departing from the spirit of the invention. Accordingly, the present invention has been described in several preferred embodiments by way of illustration, rather than limitation.

We claim:

1. An apparatus for pipeline integrity monitoring comprising:
    a magnetically permeable backing bar having a first end and a second end, the first end and the second end further defining a central portion therebetween;
    a first magnet, having a first magnetizing field strength and a first polarity, positioned proximate to the first end and in magnetic communication with the backing bar;
    a second magnet, having a second magnetizing field strength and a second polarity, positioned proximate to the central portion and in magnetic communication with the backing bar;
    a third magnet, having a third magnetizing field strength and a third polarity, positioned proximate to the second end and in magnetic communication with the backing bar; and wherein:
    the second magnetizing field strength is greater than the first magnetizing field strength; and
    the third magnetizing field strength is less than the second magnetizing field strength.

2. The apparatus of claim 1, wherein:
    the second polarity is opposite the first polarity; and
    the third polarity is the same as the first polarity.

3. The apparatus of claim 1, wherein:
    the first magnet, the second magnet, and the third magnet are adapted and positioned to induce:
    a first resultant field having a strength greater than 120 Oersted; and
    a second resultant field having a strength between 40 and 80 Oersted.

4. The apparatus of claim 3, wherein a distance between the first magnet and the second magnet is such that a resultant field is induced suitable for detecting a reduced metal-related anomaly and a distance between the second magnet and the third magnet is such that a resultant field is induced suitable for detecting a mechanically-worked-related anomaly.

5. The apparatus of claim 3, further comprising a first sensor positioned to sense MFL less than 1,000 Gauss.

6. The apparatus of claim 5, further comprising a second sensor positioned to sense MFL less than 500 Gauss.

7. A method of performing integrity monitoring of a pipeline, the method comprising the steps of:
inserting the apparatus of claim 1 into a pipeline;
traversing the apparatus through at least a portion of the pipeline;
inducing at least a first resultant field having a strength greater than 120 Oersted; and
inducing at least a second resultant field having a strength between 40 and 80 Oersted.

8. The method of claim 7, further comprising:
sensing MFL less than 1,000 Gauss.

9. The method of claim 8, further comprising;
sensing MFL less than 500 Gauss.

10. A method of detecting anomalies in a magnetically permeable object, comprising the steps of:
placing the apparatus of claim 1 in proximity to the object such that a plurality of resultant field strengths are induced in the object; and
sensing MFL resulting from anomalies.

11. The method of claim 10, wherein the plurality of resultant field strengths comprises:
a first resultant field strength sufficient to induce a resultant field suitable for detecting a reduced metal-related anomaly; and
second resultant field strength sufficient to induce a resultant field suitable for detecting a mechanically-worked-related anomaly.

12. The method of claim 11, wherein:
the first resultant field strength is greater than 120 Oersted; and
the second resultant field strength is between 40 and 80 Oersted.

13. An apparatus for detecting anomalies in a magnetically-permeable object comprising:
a magnetically-permeable backing bar; and
at least three magnets; and wherein:
the at least three magnets are in magnetic communication with the backing bar and are adapted and positioned to induce a plurality of resultant fields; and wherein:
the plurality of induced resultant fields comprises:
a first induced resultant field having a strength greater than 120 Oersted; and
a second induced resultant field having a strength between 40 and 80 Oersted.

14. The apparatus of claim 13, wherein the magnetically-permeable object comprises a pipeline wall.

15. An apparatus for detecting anomalies in a magnetically-permeable object comprising:
a magnetically-permeable backing bar; and
at least three magnets; and wherein:
the at least three magnets are in magnetic communication with the backing bar and are adapted and positioned to induce a plurality of resultant fields; and wherein:
the backing bar comprises:
a first end and a second end, the first end and the second end further defining a central portion therebetween; and
the at least three magnets comprises:
a first magnet, having a first magnetizing field strength and a first polarity, positioned proximate to the first end and in magnetic communication with the backing bar;
a second magnet, having a second magnetizing field strength and a second polarity, positioned proximate to the central portion and in magnetic communication with the backing bar;
a third magnet, having a third magnetizing field strength and a third polarity, positioned proximate to the second end and in magnetic communication with the backing bar; and wherein:
the second magnetizing field strength is greater than the first magnetizing field strength; and
the third magnetizing field strength is less than the second magnetizing field strength.

16. An apparatus for detecting anomalies in a magnetically-permeable object comprising:
a magnetically-permeable backing bar; and
at least three magnets; and wherein:
the at least three magnets are in magnetic communication with the backing bar and are adapted and positioned to induce a plurality of resultant fields; and wherein:
the magnetically permeable backing bar comprises:
a first segment having a first end and a second end;
a second segment having a first end and a second end, the first end articulably connected to the second end of the first segment; and
a third segment having a first end and a second end, the first end articulably connected to the second end of the first segment; and wherein:
the at least three magnets comprises:
a first magnet, having a first magnetizing field strength and a first polarity, positioned proximate to the first end of the first backing bar segment;
a second magnet, having a second magnetizing field strength and a second polarity, positioned proximate to the second end of the second backing bar segment;
a third magnet, having a third magnetizing field strength and a third polarity, positioned proximate to the second end of the third backing bar segment;
a fourth magnet, having a fourth magnetizing field strength and a fourth polarity, positioned proximate to the first end of the second backing bar segment;
a fifth magnet, having a fifth magnetizing field strength and a fifth polarity, positioned proximate to the first end of the third backing bar segment; and
a sixth magnet, having a sixth magnetizing field strength and a sixth polarity, positioned proximate to the second end of the first backing bar segment; and wherein:
the sum of the fourth magnetizing field strength, the fifth magnetizing field strength, and the sixth magnetizing field strength is greater than the first magnetizing field strength; and
the sum of the second magnetizing field strength and the third magnetizing field strength is less than the sum of the fourth magnetizing field strength, the fifth magnetizing field strength, and the sixth magnetizing field strength; and wherein:
the fourth polarity, the fifth polarity, and the sixth polarity are opposite the first polarity; and
the second polarity and the third polarity are the same as the first polarity.

17. The apparatus of claim 16, wherein the plurality of induced resultant fields comprises:
a first induced resultant field having a strength greater than 120 Oersted; and a second induced resultant field having a strength between 40 and 80 Oersted.

18. The apparatus of claim 17, wherein the magnetically permeable object comprises a pipeline wall.

19. The apparatus of claim 16, wherein:
the first segment and the second segment define a first inter-pole gap of less than one inch; and
the first segment and the third segment define a second inter-pole gap of less than one inch.

20. The apparatus of claim 19, wherein:
the first inter-pole gap is less than one-half inch; and
the second inter-pole gap is less than one-half inch.

21. The apparatus of claim 19, wherein:
the plurality of induced resultant fields comprises a first and a at least a second induced resultant field, the first and at least the second induced resultant fields defining at least one magnetic null; and wherein:
the first inter-pole gap is positioned proximate to the at least one magnetic null; and
the second inter-pole gap is positioned proximate to the at least one magnetic null.

22. An apparatus for detecting anomalies in a magnetically-permeable object comprising:
a magnetically-permeable backing bar; and
at least three magnets; wherein:
the at least three magnets are in magnetic communication with the backing bar and are adapted and positioned to induce a plurality of resultant fields; and wherein:
the magnetically-permeable backing bar comprises:
a first segment having a first end and a second end; and
a second segment having a first end and a second end, the first end articulably connected to the second end of the first segment; and wherein:
the at least three magnets comprises:
a first magnet, having a first magnetizing field strength and a first polarity, positioned proximate to the first end of the first backing bar segment;
a second magnet, having a second magnetizing field strength and a second polarity, positioned proximate to the second end of the first backing bar segment;
a third magnet, having a third magnetizing field strength and a third polarity, positioned proximate to the first end of the second backing bar segment; and
a fourth magnet, having a fourth magnetizing field strength and a fourth polarity, positioned proximate to the second end of the second backing bar segment; and wherein:
the sum of the second magnetizing field strength and the third magnetizing field strength is greater than the first magnetizing field strength; and
the fourth field magnetizing strength is less than the sum of the second magnetizing field strength and the third magnetizing field strength; and wherein:
the second polarity and the third polarity are opposite the first polarity; and
the fourth polarity is the same as the first polarity.

23. The apparatus of claim 22, wherein the plurality of induced resultant fields comprises:
a first induced resultant field having a strength greater than 120 Oersted; and
a second induced resultant field having a strength between 40 and 80 Oersted.

24. The apparatus of claim 23, wherein the magnetically-permeable object comprises a pipeline wall.

25. The apparatus of claim 22, wherein the first segment and the second segment define an inter-pole gap of less than one inch.

26. The apparatus of claim 25, wherein the inter-pole gap is less than one-half inch.

27. The apparatus of claim 25, wherein:
the plurality of resultant fields comprises at least a first and a second resultant field, the at least first and second resultant fields defining at least one magnetic null; and wherein the inter-pole gap is positioned proximate to the at least one magnetic null.

* * * * *